(12) United States Patent
Schulz

(10) Patent No.: US 7,923,995 B2
(45) Date of Patent: Apr. 12, 2011

(54) SENSOR COIL ARRAY FOR MAGNETIC INDUCTANCE TOMOGRAPHY WITH REDUCED MUTUAL COIL COUPLING

(75) Inventor: Volkmar Schulz, Wuerselen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 247 days.

(21) Appl. No.: 12/376,582

(22) PCT Filed: Aug. 7, 2007

(86) PCT No.: PCT/IB2007/053107
§ 371 (c)(1),
(2), (4) Date: Feb. 6, 2009

(87) PCT Pub. No.: WO2008/018018
PCT Pub. Date: Feb. 14, 2008

(65) Prior Publication Data
US 2010/0181998 A1    Jul. 22, 2010

(30) Foreign Application Priority Data
Aug. 11, 2006   (EP) .................................... 06118774

(51) Int. Cl.
*G01N 27/72* (2006.01)
*H01F 5/00* (2006.01)
(52) U.S. Cl. ......... 324/243; 324/239; 336/200; 336/206
(58) Field of Classification Search ............. 324/207.15, 324/207.17, 239, 243, 256–258; 336/200, 336/206
See application file for complete search history.

(56) References Cited

U.S. PATENT DOCUMENTS

| | | | |
|---|---|---|---|
| 5,144,236 | A | 9/1992 | Strenk |
| 5,825,164 | A | 10/1998 | Williams |
| 2002/0123694 | A1 | 9/2002 | Organ et al. |
| 2005/0253582 | A1 | 11/2005 | Giaquinto et al. |

FOREIGN PATENT DOCUMENTS

| | | |
|---|---|---|
| EP | 1521094 A1 | 4/2005 |
| WO | 8905115 A1 | 6/1989 |
| WO | 2004026136 A1 | 4/2004 |
| WO | 2005124380 A2 | 12/2005 |

OTHER PUBLICATIONS

Watson S et al: "A comparison of sensors for minimizing the primary signal in planar-array magnetic induction tomography; Comparison of sensors for minimizing the primary signal in planar-array MIT" Physiological Measurement, Institute of Physics Publishing, Bristol, GB, vol. 26, No. 2, Apr. 1, 2005, pp. S319-S331, XP020092171 ISSN: 0967-3334.

Yu Z Z et al: "Electromagnetic inductance tomography (EMT): sensor, electronics and image reconstruction algorithm for a system with a rotatable parallel excitation field" IEE Proceedings: Science, Measurement amd Technology, IEE, Stevenage, Herts, GB, vol. 145, No. 1, Jan. 6, 1998, pp. 20-25, XP006011490 ISSN: 1350-2344.

*Primary Examiner* — Bot L LeDynh
(74) *Attorney, Agent, or Firm* — Larry Liberchuk

(57) ABSTRACT

This invention relates to magnetic inductance tomography, and in particular, to coils of a sensor/driver coil array for use in a magnetic inductance tomography apparatus, in which driver/sensor coils are used to measure the induced flux in a conductive, dielectric and permittivity body, such as the human body. The sensor/driver coil array comprises at least one layer of thin coils whose centers are arranged on a regular grid, with adjacent coils overlapped by a suitable distance to cancel inductive neighbor coupling between them.

8 Claims, 3 Drawing Sheets possible setup suitable for a fully planar MIT.

Bridging capacitors in order to reduce the
growth of the inductive voltage along the wires.

SENSOR COIL ARRAY FOR MAGNETIC INDUCTANCE TOMOGRAPHY WITH REDUCED MUTUAL COIL COUPLING

This invention relates to magnetic inductance tomography, and in particular, to coils for use in a magnetic inductance tomography apparatus, in which driver/sensor coils are used to measure the induced flux in a conductive, dielectric and permittivity body, such as the human body.

In order to investigate pathological conditions in a human body, various non-invasive techniques have previously been proposed, such as X-ray tomography, and electrical impedance tomography, in which the distribution of impedance in a cross-section of a living body is measured by attaching a series of electrodes through which small currents are passed. Further pairs of sensing electrodes are then used to make potential difference measurements, providing data from which images can be constructed.

A similar method of measuring impedance distribution, which avoids the direct attachment of sensors, is to use sets of driver/sensing coils to induce a magnetic flux in the conductive, dielectric body, and to then measure the results of induced flux. This technique is known as magnetic inductance tomography (MIT).

MIT unlike EIT does not require electrical contacts with the body and uses interaction of oscillating magnetic field with conductive media. The field, which can be excited and registered by small coils arranged around the object, is perturbed by eddy currents in the object. The conductivity (and permittivity) can be reconstructed from the measurements of perturbed field outside the object. Although the approximated equation for vector potential in case of MIT is very similar to the equation for scalar potential in case of EIT, there are important differences in solving corresponding inverse problems. The first experimental measuring system for MIT with 16 transmitting and receiving coils has been built and tested recently in the laboratory.

In order to apply the magnetic field to the human body and to sense the perturbed field, it is necessary to provide suitable arrays of signal coils, supported in a structure which is preferably flexible. Such arrangements have previously been used as signal coil arrays in MRI machines and one example is shown in Philips WO/05124380.

A problem which arises in utilising coil systems of this kind, however, is that most of the magnetic flux of the excitation coil is directly coupled to that of adjacent receiver coils, and consequently the received signal is dominantly affected by the direct coupling, instead of the coupling generated due to the actual human body itself (i.e. electrical conductivity and permittivity of the biological tissue). The direct coupling therefore limits the sensitivity of the entire system.

It is, of course, possible to use a gradiometer to measure the variations in the magnetic field caused by direct coupling, but these add considerably to the bulk and complication of the overall set up.

Accordingly, the present invention provides a sensor/driver coil array for use in magnetic inductance tomography comprising at least one layer of thin coils whose centres are arranged on a regular grid, with adjacent coils overlapped by a suitable distance to cancel inductive neighbour coupling between them.

The spacing between adjacent coils is set a way that no voltage is induced in a particular coil, while the adjacent coil is driven. That is to say, the overlap between peripheral conductors is such that any voltage induced by the conductors of one coil is completely cancelled by the counter EMF in the windings of the adjacent coil.

It will be appreciated that all the coils may be etched on a single PCB, which can be flexible to facilitate use in close proximity to the human body.

Some embodiments of the invention will now be described, by way of example, with reference to the accompanying drawings in which.

Figure 1:
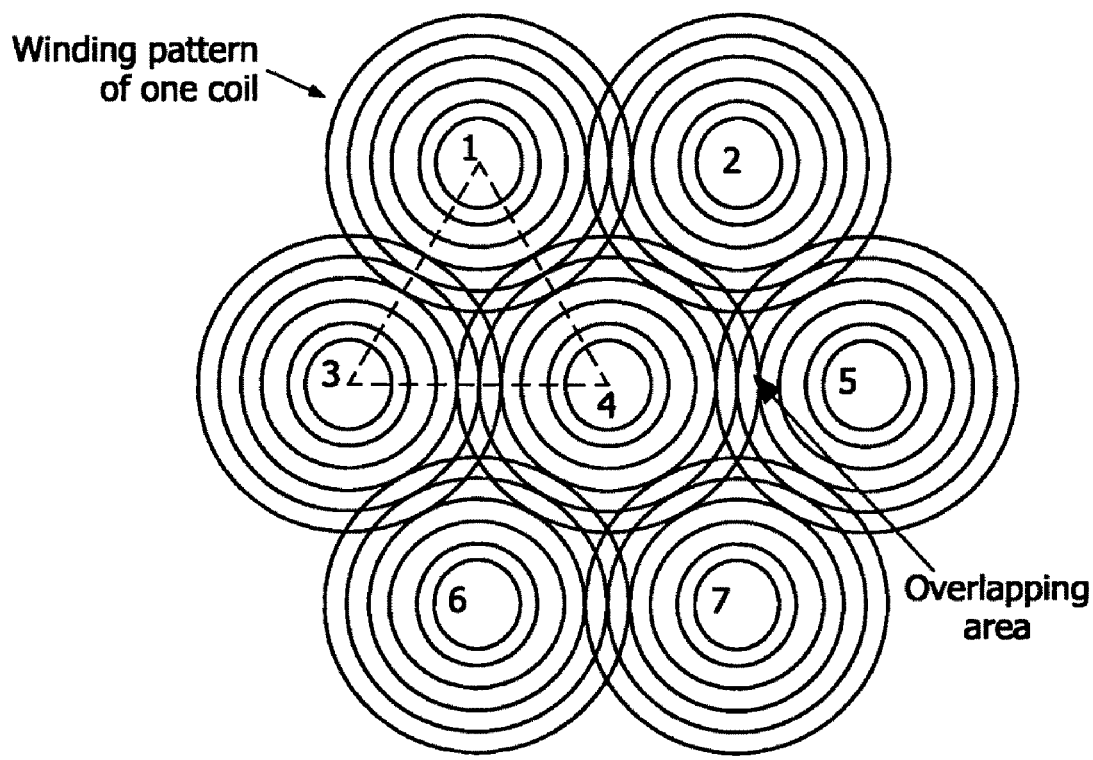
FIG. 1 is a plan view of a simple coil arrangement according to the invention.

FIG. 1 shows a simplified structure containing 7 coils. All coils are identical and could have several thin layers if necessary (e.g. for low frequency MIT). For simplicity coils with circular windings are shown and the alternations from the outer to the inner windings are omitted in this figure. The centre points of the coils are located on an equilateral grid as shown by the dashed triangle, although they could of course be arranged in various other patterns such as a square grid. The distance of the coils is determined by the requirement that no voltage is induced in a coil, while the neighbour coil is driven.

In other words the distance is chosen to have neighbour coils inductively decoupled from each other. For a setup in FIG. 1, coil 4 is inductively decoupled from all the other coils, while e.g. coil 1 is decoupled from coils 2, 3 and 4. In practice the required positions are determined by measuring the induced voltage in one coil whilst applying a voltage to the other while moving one relative to the other.

The coupling matrix (or K-matrix) of the structure of FIG. 1 is shown in equation (1):

$$K = \begin{bmatrix} 1 & 0 & 0 & 0 & k_{15} & k_{16} & k_{17} \\ 0 & 1 & k_{25} & 0 & 0 & k_{26} & k_{27} \\ 0 & k_{32} & 1 & 0 & k_{35} & 0 & k_{37} \\ 0 & 0 & 0 & 1 & 0 & 0 & 0 \\ k_{51} & 0 & k_{53} & 0 & 1 & k_{56} & 0 \\ k_{61} & k_{62} & 0 & 0 & k_{65} & 1 & 0 \\ k_{71} & k_{72} & k_{73} & 0 & 0 & 0 & 1 \end{bmatrix},$$

$$L_d = \begin{bmatrix} L_1 & 0 & 0 & 0 & 0 & 0 & 0 \\ 0 & L_2 & 0 & 0 & 0 & 0 & 0 \\ 0 & 0 & L_3 & 0 & 0 & 0 & 0 \\ 0 & 0 & 0 & L_4 & 0 & 0 & 0 \\ 0 & 0 & 0 & 0 & L_5 & 0 & 0 \\ 0 & 0 & 0 & 0 & 0 & L_6 & 0 \\ 0 & 0 & 0 & 0 & 0 & 0 & L_7 \end{bmatrix}$$

$L_d$ is the matrix of self inductances. It will be seen that there are large number of zero elements in the K-matrix. The overall impedance matrix of the system is given by equation (2).

$$Z = j\omega L + R_d + \frac{1}{j\omega}C^{-1} \text{ with } L = \sqrt{L_d}\, K \sqrt{L_d} \qquad (2)$$

When there is no tissue located close of the coil array, $R_d$ is a diagonal matrix containing the self-resistances of the coils. Thus resistive coupling from element to elements can be neglected. For low frequency, capacitive coupling can also be neglected, which leads to an impedance matrix of equation (3).

$$Z = j\omega L + R_d \quad (3)$$

Figure 2:
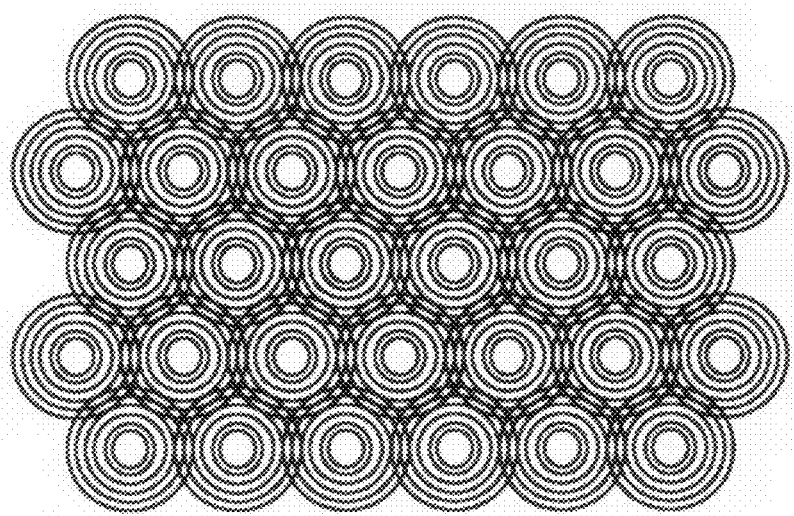
FIG. 2 shows a coil arrangement for a fully planar 32 channel system.

FIG. 2 shows the arrangement of coils for a system fully planar 32-channel system. If the lateral extension of the coils is small compared to the bending radius of the printed circuit board, where the coils are mounted, the decoupling will stay stable. This allows a placement of the coil array closer to the body, e.g. in clothes.

Figure 3:
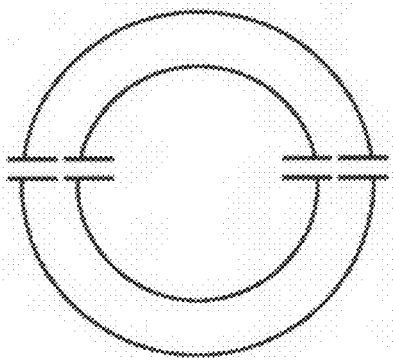
FIG. 3 illustrates diagrammatically an arrangement of bridging capacitors.

For higher frequencies and lower distance of the sensor to the human body, capacitive coupling between the coils and the coils to the tissue should be kept as low as possible. Thus, bridging capacitors are placed at intervals as shown in FIG. 3, to avoid the increase of voltage between the windings, and thus outer electrical field, i.e. to compensate for the inductive reactance. All capacitors will have the same value and will lead to a pure real input impedance of on coil (self resonant setup). The higher the frequency, the more capacitors should be used.

Figure 4:
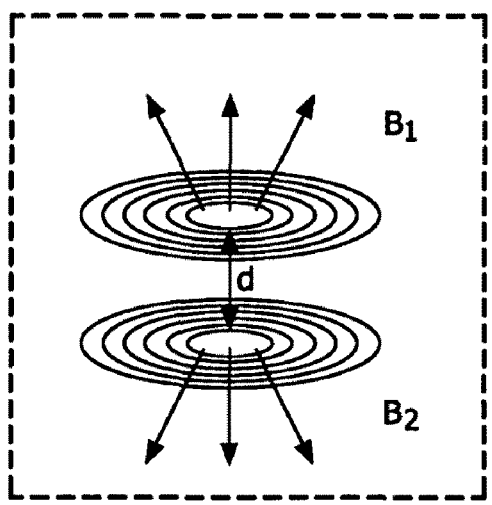
FIG. 4 shows a "double-layer" coil arrangement.
Figure 5:
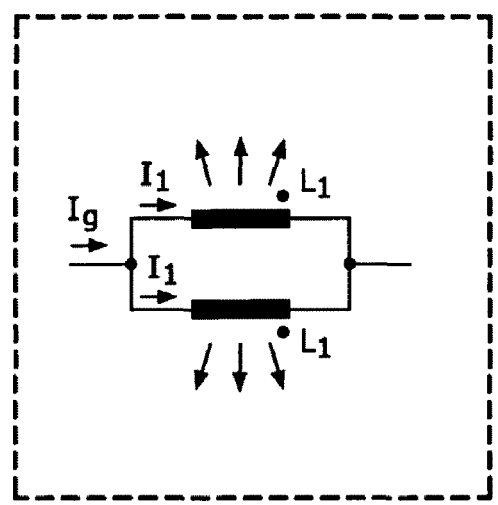
FIG. 5 is an equivalent circuit of the arrangement of FIG. 4.

FIG. 4 illustrates the principle of a two-layer coil system in which the coils are arranged in superimposed pairs. The basic idea of the two coils design is that the field $B_1$ produced by the upper coil is compensated via an additional lower coil producing $B_2$ that is located at a certain spacing d from the upper coil. FIG. 5 shows the equivalent circuit of such coil, consisting of two anti-parallel connected coils. Those coils will compensate for some distance and thus form a sensor that is less sensitive to electromagnetic radiation in the surroundings at the cost of some reduction in overall sensitivity. This arrangement also helps to reduce "next-next-coupling" in an array (i.e. coupling to the next coil but one) which is good for the overall MIT procedure.

Since the sensor array can be made very thin, and avoids the need for extra sensing devices such as gradiometers, it can be incorporated in an easily portable sensor pad and used "in-situ" for example in a patient's bed, or in an item of clothing. In addition, of course, it may be used in conjunction with apparatus such as an MRI machine, to provide additional exciting/sensing coils, closely positioned to a patient's body.

The invention claimed is:

1. A sensor/driver coil array for use in magnetic inductance tomography comprising two layers of thin coils, each layer comprising a plurality of thin coils whose centres are arranged on a regular grid, with adjacent coils in a layer being overlapped by a suitable distance to cancel inductive neighbour coupling between them, and wherein each coil in the first layer is paired with a respective coil in the second layer and the pairs of coils are anti-parallel connected and arranged at such a distance apart that they compensate each others' fields and thereby reduce external coupling effects.

2. A coil array according to claim 1 in which the coils are wound from wire.

3. A coil array according to claim 1 in which the coils are etched on a single printed circuit board.

4. A coil array according to claim 3 in which the PCB is flexible.

5. A coil array according to claim 1 in which each coil includes a plurality of capacitors connected in series at intervals along the winding to compensate for the voltage drop produced by the inductive reactance in that coil.

6. A coil array according to claim 1 in which the array is embedded in a wearable garment so that the coil signals can be applied in close proximity to the patient's body.

7. A coil array according to claim 1 in which all the coils have the same winding pattern.

8. A sensor/driver coil array according to claim 1 in which all coils are located regularly, by N coils, with N=1 or 2 neighbour coils for a line-structure, N=3, N=4 or N=6 neighbour coils for a surface structure.

* * * * *